United States Patent [19]

Bertram et al.

[11] Patent Number: 5,095,032
[45] Date of Patent: Mar. 10, 1992

[54] PARASITICIDAL NEW SUBSTITUTED THIENOPYRANONES

[75] Inventors: Heinz-Jürgen Bertram, Bonn; Nikolaus Müller, Monheim; Achim Harder, Leverkusen, all of Fed. Rep. of Germany

[73] Assignee: Bayer Aktiengesellschaft, Leverkusen, Fed. Rep. of Germany

[21] Appl. No.: 555,553

[22] Filed: Jul. 19, 1990

[30] Foreign Application Priority Data

Aug. 3, 1989 [DE] Fed. Rep. of Germany ....... 3925719

[51] Int. Cl.$^5$ .................... A61K 31/38; C07D 495/02
[52] U.S. Cl. ..................... 514/443; 549/50
[58] Field of Search .......................... 549/50; 514/443

[56] References Cited

U.S. PATENT DOCUMENTS 587,786  2/1976  Pankavich ........................... 514/457

FOREIGN PATENT DOCUMENTS 0241834  4/1987  European Pat. Off. .
3012642  10/1981  Fed. Rep. of Germany .
3613065  10/1987  Fed. Rep. of Germany .

OTHER PUBLICATIONS

Mladenovic and Castro, "Cu(I) Substitutions . . .", Dept. Nematology, Univ. Calif., J. Helero Chem., vol. 5, No. 2, pp. 227–230 (4–1968).
Recueil Des Travaup Chimiques Des, Pays-Bas, Band 86, No. 10, Oct. 10, 1967, pgs. 971-974, Den Haag, NL; T. Kralt.

Primary Examiner—C. Warren Ivy
Assistant Examiner—Catherine Scalzo
Attorney, Agent, or Firm—Sprung Horn Kramer & Woods

[57] ABSTRACT

Parasiticidal new substituted thienopyranones of the formula

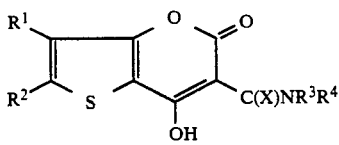

in which
X represents O or S,
$R^1$ and $R^2$ independently of one another represent hydrogen, halogen, CN, $NO_2$, alkyl, aralkyl, aryl, alkylcarbonyl or alkoxycarbonyl, or, together with the adjacent C atoms, form a carbocyclic ring which is optionally interrupted by heteroatoms,
$R^3$ represents optionally substituted alkyl or phenyl,
$R^4$ represents hydrogen or alkyl,
$R^3$ and $R^4$, together with the adjacent nitrogen atom, represent a heterocyclic 5- or 6-membered ring.

Some of the intermediates for making them are also new.

5 Claims, No Drawings

PARASITICIDAL NEW SUBSTITUTED THIENOPYRANONES

The present invention relates to new substituted thienopyranones, to a process for their preparation and to their use against parasites.

3-Carbamoyl-4-hydroxycoumarins and their action against pests and parasites have already been disclosed (DE-OS German Published Specification) 3,012,642; 3,613,065 published; U.S. Pat. application No. B 587,786). However, the action of these compounds is not satisfactory in every case.

The present invention relates to:

1. The new substituted thienopyranones of the formula I

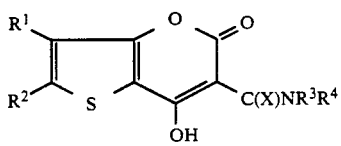

in which
- X represents O or S,
- $R^1$ and $R^2$ independently of one another represent hydrogen, halogen, CN, $NO_2$, alkyl, aralkyl, aryl, alkylcarbonyl or alkoxycarbonyl, or, together with the adjacent C atoms, form a carbocyclic ring which is optionally interrupted by heteroatoms,
- $R^3$ represents optionally substituted alkyl or phenyl,
- $R^4$ represents hydrogen or alkyl,
- $R^3$ and $R^4$, together with the adjacent nitrogen atom, represent a heterocyclic 5- or 6-membered ring.

2. Process for the preparation of the new substituted thienopyranones of the formula I

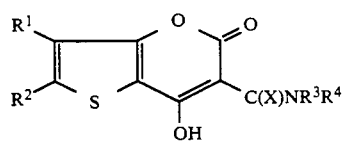

in which
- X represents O or S,
- $R^1$ and $R^2$ independently of one another represent hydrogen, halogen, CN, $NO_2$, alkyl, aralkyl, aryl, alkylcarbonyl or alkoxycarbonyl, or, together with the adjacent C atoms, form a carbocyclic ring which is optionally interrupted by heteroatoms,
- $R^3$ represents optionally substituted alkyl or phenyl,
- $R^4$ represents hydrogen or alkyl,
- $R^3$ and $R^4$, together with the adjacent nitrogen atom, represent a heterocyclic 5- or 6-membered ring, characterized in that a) in the case in which $R^4$ represents hydrogen in formula I, thienopyranones of the formula II

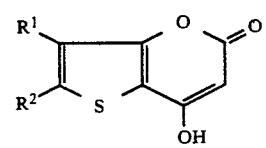

in which $R^1$ and $R^2$ have the abovementioned meanings, are reacted with iso(thio)cyanates of the formula III $$X=C=N-R^3 \qquad III$$

in which
$R^3$ and X have the abovementioned meanings, or b) compounds of the formula IV

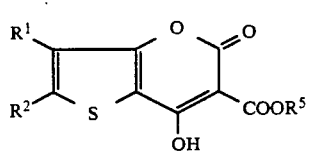

in which
$R^1$ and $R^2$ have the abovementioned meanings and
$R^5$ represents $C_{1-4}$-alkyl, are reacted with amines of the formula V $$H N R^3 R^4 \qquad V$$

in which
$R^3$ and $R^4$ have the abovementioned meanings, or c) compounds of the formula II

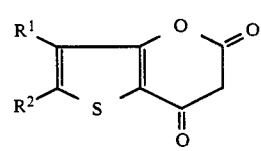

in which
$R^1$ and $R^2$ have the abovementioned meanings, are reacted with (thio)-carbamoyl chlorides of the formula VI

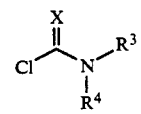

in which
X, $R^3$ and $R^4$ have the abovementioned meanings.

3. Compounds of the formula IV

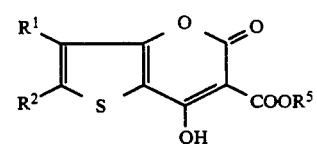

in which
$R^1$, $R^2$ and $R^5$ have the meanings indicated under (2), are new.

4. Process for the preparation of the compounds of the formula IV according to (3) above, characterized in that compounds of the formula II

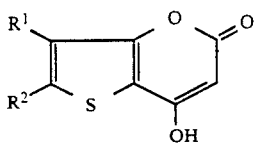

II in which
R¹ and R² have the abovementioned meanings, are reacted with chloroformic acid esters of the formula VII Cl—COOR⁵    VII in which
R⁵ represents $C_{1-4}$-alkyl.

Preferred compounds of the formula I are those in which
R¹ and R² represent hydrogen, halogen such as fluorine, chlorine or bromine, CN, NO₂, $C_{1-6}$-alkyl, optionally substituted benzyl, $C_{1-4}$-alkylcarbonyl, $C_{1-4}$-alkoxycarbonyl or optionally substituted phenyl, or, together with the adjacent C atoms represent a carbocyclic 5-, 6- or 7-membered ring which may optionally also be interrupted by O, N or S, R³ represents optionally substituted $C_{1-6}$-alkyl or optionally substituted phenyl, R⁴ represents hydrogen or $C_{1-4}$-alkyl and R³ and R⁴, together with the adjacent N atom, represent pyrrolidine, piperidine, piperazine or morpholine.

Preferred substituents for phenyl which may be mentioned are:
alkyl preferably having 1 to 4, in particular 1 or 2 carbon atoms, such as methyl, ethyl, n.- and i.-propyl and n.-, i.-, s.- and t.-butyl; alkoxy preferably having 1 to 4, in particular 1 or 2 carbon atoms, such as methoxy, ethoxy, n.- and i.-propyloxy and n.-, i.-, s.-and t.-butyloxy; alkylthio preferably having 1 to 4, in particular 1 or 2 carbon atoms, such as methylthio, ethylthio, n.- and i.-propylthio and n.-, i.-, s.- and t.-butylthio; halogenoalkyl preferably having 1 to 4, in particular 1 or 2 carbon atoms and preferably 1 to 5, in particular 1 to 3 halogen atoms, the halogen atoms being identical or different and, as halogen atoms, preferably being fluorine, chlorine or bromine, in particular fluorine, such as trifluoromethyl, fluoroethyl or chloroethyl; halogenoalkoxy preferably having 1 to 4, in particular 1 or 2 carbon atoms and preferably 1 to 5, in particular 1 to 3 halogen atoms, the halogen atoms being identical or different and, as halogen atoms, preferably being fluorine, chlorine or bromine, in particular fluorine, such as trifluoromethoxy; halogenoalkylthio preferably having 1 to 4, in particular 1 or 2 carbon atoms and preferably 1 to 5, in particular 1 to 3 halogen atoms, the halogen atoms being identical or different and, as halogen atoms, preferably being fluorine, chlorine or bromine, in particular fluorine, such as trifluoromethylthio; alkylenedioxy preferably having 1 or 2 carbon atoms such as methylenedioxy or ethylenedioxy; halogen-substituted alkylenedioxy preferably having 1 or 2 carbon atoms and preferably 1 to 4, in particular 2 or 3 halogen atoms, the halogen atoms being identical or different and, as halogen atoms, preferably being fluorine or chlorine, in particular fluorine, such as difluoromethylenedioxy, trifluoroethylenedioxy or tetra- fluoroethylenedioxy. Further substituents are halogen, preferably fluorine, chlorine, bromine and iodine, in particular chlorine and bromine; cyano; nitro; dialkylamino preferably having 1 to 4, in particular 1 or 2 carbon atoms per alkyl group, such as dimethylamino, diethylamino or methyl-n.-butyl-amino; alkylcarbonyl preferably having 2-4 carbon atoms; carbalkoxy preferably having 2 to 4, in particular 2 or 3 carbon atoms, such as carbomethoxy and carboethoxy; alkylsulphonyl preferably having 1 to 4, in particular 1 or 2 carbon atoms, such as methylsulphonyl and ethylsulphonyl; arylsulphonyl preferably having 6 or 10 aryl carbon atoms, such as phenylsulphonyl; or phenyl, naphthyl, phenoxy, naphthoxy, phenylthio or naphthylthio which, for their part, may again be substituted by one of the abovementioned substituents.

Preferred substituents for alkyl which may be mentioned are:
halogen, in particular chlorine, bromine or fluorine, and $C_{1-4}$-alkoxy, in particular methoxy or ethoxy.

Particularly preferred compounds of the formula I are those in which
R¹ and R² represent hydrogen, chlorine, bromine, CN, $C_1$–$C_4$-alkyl such as methyl, ethyl, i-propyl or t-butyl, optionally substituted phenyl, acetyl, methoxycarbonyl or ethoxycarbonyl, or, together with the adjacent C atoms represent a 5- or 6-membered ring, R³ represents optionally substituted phenyl, and R⁴ represents hydrogen.

Particularly preferred substituents for phenyl are:
$C_1$-$C_4$-alkyl, in particular methyl, ethyl, $C_1$-$C_4$-alkoxy, in particular methoxy or ethoxy, $C_1$-$C_4$-halogenoalkoxy, in particular trifluoromethoxy or fluorochloroethoxy, $C_1$-$C_4$-halogenoalkylthio, in particular trifluoromethylthio or fluorochloromethylthio, $C_1$-$C_4$-alkylthio, in particular methylthio, halogenosulphonyl, in particular fluorosulphonyl or chlorosulphonyl, $C_1$-$C_4$-alkylsulphonyl, in particular methylsulphonyl, $C_1$-$C_4$-halogenoalkylsulphonyl, in particular trifluoromethylsulphonyl, $C_1$-$C_4$-halogenoalkyl, in particular trifluoromethyl, or methylenedioxy or ethylenedioxy which are optionally substituted by fluorine or chlorine, halogen, in particular fluorine or chlorine, CN, NO₂, or phenoxy which is optionally substituted by one of the abovementioned radicals.

Very particularly preferred compounds of the formula I are those in which
X represents oxygen,
R¹ represents hydrogen,
R² represents phenyl which is optionally substituted by halogen such as chlorine, fluorine or bromine, $C_{1-4}$-alkyl such as methyl, $C_{1-4}$-halogenoalkyl such as trifluoromethyl, or $C_{1-4}$-alkoxy such as methoxy, or R¹ and R², together with the adjacent C atoms, represent a 5-membered ring,
R³ represents phenyl which is optionally substituted by halogen such as chlorine, fluorine or bromine, $C_{1-4}$-alkyl such as methyl, $C_{1-4}$-halogenoalkyl such as trifluoromethyl, $C_{1-4}$-alkoxy such as methoxy, $C_{1-4}$-alkylmercapto such as methylmercapto, $C_{1-4}$-halogenoalkylmercapto such as trifluoromethylmercapto, or $C_{1-4}$-alkoxycarbonyl such as methoxycarbonyl, and
R⁴ represents hydrogen.

In particular, the following compounds of the formula I may be mentioned in which the radicals R¹, R², R³, R⁴ and X have the meanings indicated:

| X | $R^1$ | $R^2$ | $R^3$ | $R^4$ |
|---|---|---|---|---|
| O | H | H | H | 4-trifluoromethylphenyl |
| O | H | H | H | 4-trifluoromethylmercaptophenyl |
| O | H | H | H | 3-chloro-4-trifluoromethoxy-phenyl |
| O | H | H | H | 3-fluorosulphonylphenyl |
| O | H | H | H | 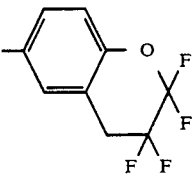 |
| O | H | H | H | 4-(3'-trifluoromethylphenoxy)-phenyl |
| O | H | H | H | 4-fluoro |
| O | H | H | H | 4-methylmercaptophenyl |
| O | $CH_3$ | H | H | 4-chlorophenyl |
| O | $CH_3$ | H | H | 4-methylphenyl |
| S | H | H | H | 4-chlorophenyl |
| O | H | $CH_3$ | H | 4-chlorophenyl |
| O | H | $CH_3$ | H | 4-methylphenyl |
| O | F | H | H | 4-chlorophenyl |
| O | F | H | H | 3,4-dichlorophenyl |
| O | Cl | H | H | 4-chlorophenyl |
| O | Cl | H | H | 3,4-dichlorophenyl |
| O | H | F | H | 4-chlorophenyl |
| O | H | F | H | 3,4-dichlorophenyl |
| O | H | Cl | H | 3,4-dichlorophenyl |
| O | H | Cl | H | 4-chlorophenyl |
| O | H | $CH_3$ | H | 3,4-dichlorophenyl |
| O | H | $CH_3$ | H | 2-chloro-4-trifluoromethylphenyl |
| O | H | $CH_3$ | H | 4-trifluoromercaptophenyl |
| O | H | $CH_3$ | H | 4-trifluoromethoxy phenyl |
| O | H | Br | H | 4-chlorophenyl |
| O | H | Br | H | 4-Methylphenyl |
| O | Br | Br | H | 4-chlorophenyl |
| O | Br | $CH_3$ | H | 4-Methylphenyl |
| O | Br | $CH_3$ | H | 4-chlorophenyl |
| O | Br | $CH_3$ | H | 4-trifluoromethylmercaptophenyl |
| O | Br | $CH_3$ | H | 4-trifluoromethoxy-phenyl |
| O | Br | $CH_3$ | H | 2-chloro-4-trifluoromethylphenyl |
| O | H | phenyl | H | 4-methylphenyl |
| O | H | phenyl | H | 4-chlorophenyl |
| O | phenyl | H | H | 4-methylphenyl |
| O | phenyl | H⁻ | H | 4-chlorophenyl |
| O | $CH_3$ | phenyl | H | 4-methylphenyl |
| O | phenyl | $CH_3$ | H | 4-chlorophenyl |
| O | F | Cl | H | 4-chlorophenyl |
| O | F | Cl | H | 3,4-dichlorophenyl |
| O | F | F | H | 4-chlorophenyl |
| O | F | F | H | 3,4-dichlorophenyl |
| O | Cl | Cl | H | 4-chlorophenyl |
| O | Cl | Cl | H | 3,4-dichlorophenyl |
| O | $CH_3$ | $CH_3$ | H | 4-chlorophenyl |
| O | $CH_3$ | $CH_3$ | H | 4-methylphenyl |

If thieno-[3.2]-7-hydroxy-pyran-5-one is employed as the thienopyranone of the formula II and p-tolyl isocyanate as the compound of the formula III in process 2a), the process can be represented by the following equation:

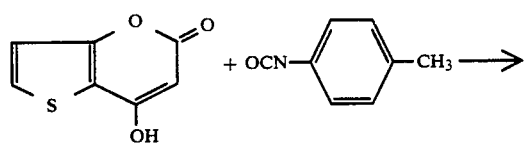

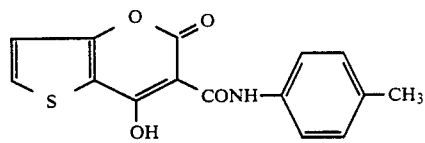

Some of the compounds of the formula II are new.
They can be prepared from 2-aceto-3-hydroxythiophenes (VIII) by processes which are known per se (T. Kralt, Recueil 86 (1967) p. 971-974).

The preparation of the 2-aceto-3-hydroxythiophenes is carried out by reaction of 2,5-dihydroxy-2,5-dimethyl-1,4-dithiene with peptide esters (compare T. Kralt, Recueil 86 (1967) p. 971-974).

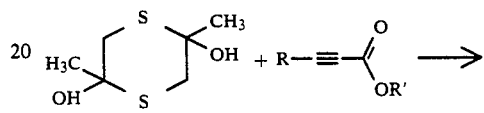

VIII

Alternatively to this, the preparation of 2-aceto-3-hydroxythiophenes is possible by reaction of β-halogen-substituted α,β-unsaturated esters with 2,5-dihydroxy-2,5-dimethyl-1,4-dithione or by reaction of β-thioxo esters with α-halogenoacetone.

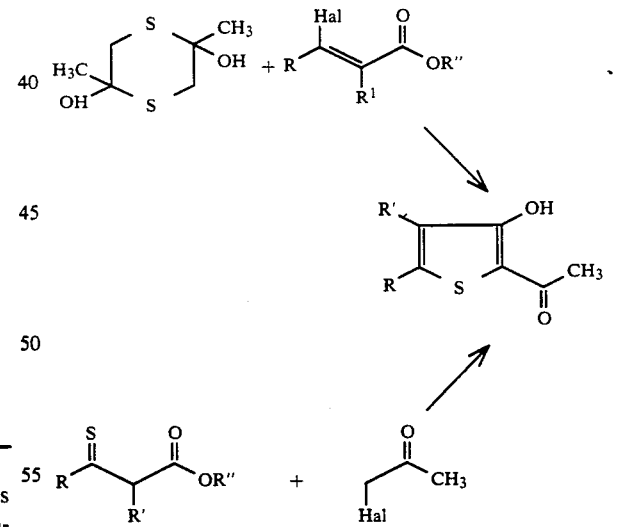

Hal = halogen or equivalent leaving group
The β-thioxo esters are known (F. Duus, Tetrahedron 28 (1972) p. 5923-5947).
Compounds of the formula III are known.
Preferably, compounds of the formulae II and III are employed in which X, $R^1$, $R^2$, $R^3$ and $R^4$ have the preferred and particularly preferred meanings indicated for the compounds of the formula I.
The following compounds of the formula II may be mentioned in particular:

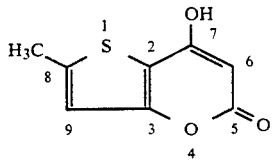

8-phenyl-thieno-[3.2]-7-hydroxypyran-5-one
8-bromo-thieno-[3.2]-7-hydroxypyran-5-one
8-chloro-thieno-[3.2]-7-hydroxypyran-5-one
8-carboethoxy-thieno-[3.2]-7-hydroxypyran-5-one
8-carbomethoxy-thieno-[3.2]-7-hydroxypyran-5-one
8-ethyl-thieno-[3.2]-7-hydroxypyran-5-one
8-methyl-9-bromo-thieno-[3.2]-7-hydroxypyran-5-one
8-ethyl-9-bromo-thieno-[3.2]-7-hydroxypyran-5-one
8-methyl-9-bromo-thieno-[3.2]-7-hydroxypyran-5-one
8-ethyl-9-chloro-thieno-[3.2]-7-hydroxypyran-5-one
8-methyl-9-chloro-thieno-[3.2]-7-hydroxypyran-5-one
9-methyl-thieno-[3.2]-7-hydroxypyran-5-one
9-ethyl-thieno-[3.2]-7-hydroxypyran-5-one
8-bromo-9-methyl-[3.2]-7-hydroxypyran-5-one
8-fluoro-thieno-[3.2.]-7-hydroxypyram-5-one
9-fluoro-thieno-[3.2.]-7-hydroxypyran-5-one
8,9-dichloro-thieno-[3.2.]-7-hydroxypyran-5-one
8,9-difluoro-thieno-[3.2.]-7-hydroxypyran-5-one
9-bromo-thieno-[3.2.]-7-hydroxypyran-5-one
8,9-dibromo-thieno[3.2.]-7-hydroxypyran-5-one
8-bromo-[3.2]-7-hydroxypyran-5-one
9-chloro-[3.2]-7-hydroxypyran-5-one
8-(4'-chlorophenyl)-thieno-[3.2]-7-hydroxypyran-5-one
8-(4'-methoxyphenyl)-thieno-[3.2]-7-hydroxypyran-5-one
8-(3'-chlorophenyl)-thieno-[3.2]-7-hydroxypyran-5-one
8-(2'-chlorophenyl)-thieno-[3.2]-7-hydroxypyran-5-one
8-(2',4'-dichlorophenyl)-thieno-[3.2]-7-hydroxypyran-5-one
8-phenyl-9-methyl-thieno-[3.2]-7-hydroxypyran-5-one
8-phenyl-9-ethyl-thieno-[3.2]-7-hydroxypyran-5-one
8-phenyl-9-bromo-thieno-[3.2]-7-hydroxypyran-5-one
8-phenyl-9-chloro-thieno-[3.2]-7-hydroxypyran-5-one The following compounds of the formula III may be mentioned in particular:
2,4-dimethylphenyl isocyanate
2,3-dimethylphenyl isocyanate
2,4,6-trimethylphenyl isocyanate
4-chloro-2-methylphenyl isocyanate
2-chloro-4-methylphenyl isocyanate
4-bromophenyl isocyanate
4-methylphenyl thioisocyanate Compounds of the formulae II and III are reacted in the presence of diluents and in the presence of bases and, if appropriate, in the presence of other catalysts.

Bases which may be mentioned are: alkali metal alkoxides, alkaline earth metal alkoxides and tertiary amines. The following bases may particularly preferably be mentioned: triethylamine, pyridine, picoline, trimethylamine, N-methylmorpholine, N-ethylpyrrolidine, diazabicyclo[4.3.0]-undecene (DBU), 1,4-diazabicyclo- 2,2,2-octane (DABCO) or diazabicyclo[3.2.0-]nonene (DBN).

All inert organic solvents are suitable as diluents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, additionally esters, such as methyl acetate and ethyl acetate, furthermore nitriles, such as, for example, acetonitrile and propionitrile, benzonitrile, glutaronitrile, and moreover amides, such as, for example, dimethylformamide, dimethylacetamide and N-methylpyrrolidone, and also dimethyl sulphoxide, tetramethylene sulphone and hexamethylphosphoramide.

Suitable catalysts are the catalysts customary for reactions with isocyanates. Those which may be mentioned are: metal catalysts of Zn, Sn or Pb such as dibutyltin dilaurate, dibutyltin dioxide, tin octoate, lead octoate, zinc octoate, zinc chloride and zinc acetate.

The reaction is carried out between 0° and 150° C., preferably between 20° and 50° C. It is preferably carried out under normal pressure.

The compounds of the formulae II and III are employed in equimolar amounts and a small excess of one or the other components confers no substantial advantages.

Working up is carried out in a manner known per se, for example by adding dilute acid to the reaction mixture, filtering off the product or separating off the organic phase and removing the solvent by distillation.

If dichlorothieno-[3.2]-7-hydroxy-6-ethoxy-carbonyl-pyran-5-one is employed as the compound of the formula IV and 4-trifluoromethoxyaniline as the compound of the formula V in process 2b), the process can be represented by the following equation:

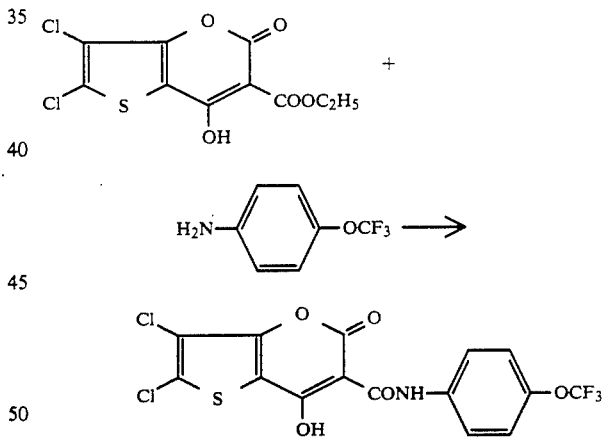

The compounds of the formula IV are new. Their preparation is described below. Compounds of the formula V are known. Preferably, compounds of the formulae IV and V are employed in which $R^1$, $R^2$, $R^3$, and $R^4$ have the preferred and particularly preferred meanings indicated for the compounds of the formula I.

The following compounds of the formula IV may be mentioned in particular:
6-carboethoxy-thieno-[3.2]-pyran-5-one
5-carbomethoxy-thieno-[3.2]-pyran-5-one The following compounds of the formula V may be mentioned in particular:
4-trifluoromethoxy aniline, 4-trifluoromethylmercaptoaniline, 3-chloro-4-trifluoromethoxy aniline, 3-chloro-4-trifluoromethylmercaptoaniline, 3-nitro-4-trifluoromethoxyaniline, 4-(1,1,2,2-tetrafluoroethoxy)-aniline, 2,6-dichloro-4-trifluoromethylmercapto-aniline, 10 4-amino-4'-trifluoromethyl-diphenyl ether, 4-amino-3'-trifluoromethyldiphenyl ether.

The reaction of the compounds of the formula IV and V is preferably carried out in the presence of diluents and in the presence of bases.

All inert organic solvents are suitable as diluents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, additionally esters, such as methyl acetate and ethyl acetate, furthermore nitriles, such as, for example, acetonitrile and propionitrile, benzonitrile, glutaronitrile, and moreover amides, such as, for example, dimethylformamide, dimethylacetamide and N-methylpyrollidone, and also dimethyl sulphoxide, tetramethylene sulphone and hexamethylphosphoramide, and furthermore alcohols such as methanol, ethanol, propanol and butanol.

Bases which may be mentioned are alkali metal hydroxides and alkaline earth metal hydroxides, and alkali metal alkoxides and alkaline earth metal alkoxides, in particular sodium methoxide or sodium ethoxide.

The reaction is carried out between 50° and 150° C., preferably between 60° and 110° C. It is preferably carried out under normal pressure.

The compounds of the formulae VI and VII are employed in equimolar amounts and a small excess of one or the other components confers no substantial advantages.

Working up is carried out in a manner known per se, for example by adding water to the reaction mixture, separating off the organic phase and removing the solvent by distillation.

If 2-methyl-7-hydroxy-thieno[3.2]propan-5-one is employed as the compound of the formula II and methyl chloroformate as the compound of the formula VI in process 4, process 4 can be represented by the following equation:

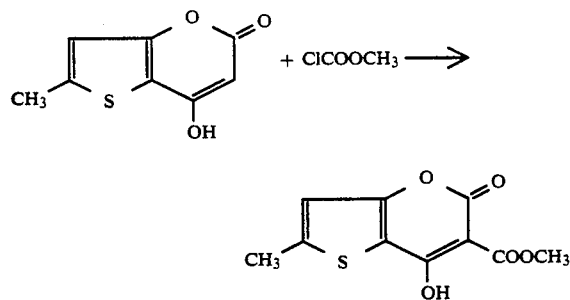

Some of the compounds of the formula II are new (see above). Compounds of the formula VI are known.

Compounds of the formula II are preferably employed in which R¹ and R² have the preferred and particularly preferred meanings indicated for the compounds of the formula I.

The abovementioned compounds of the formula II may be mentioned in particular. The following compounds of the formula VI may be mentioned in particular: methyl chloroformate ethyl chloroformate The reaction is carried out at temperatures of 20°–200° C., preferably at 50°–150° C., particularly preferably at the boiling point of the diluent.

All inert organic solvents are suitable as diluents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore alcohols such as methanol, ethanol, isopropanol and butanol, furthermore ethers such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, additionally esters, such as methyl acetate and ethyl acetate, furthermore nitriles, such as, for example, acetonitrile and propionitrile, benzonitrile, glutaronitrile, and moreover amides, such as, for example, dimethylformamide, dimethylacetamide and N-methylpyrrolidone, and also dimethyl sulphoxide, tetramethylene sulphone and hexamethylphosphoramide.

Suitable bases are inorganic and organic bases. Bases which may be mentioned are alkali metal and alkaline earth metal hydroxides, carbonates, hydrogen carbonates and alkoxides, and further amines such as, in particular, tertiary amines, for example trimethylamine, triethylamine, N-methylmorpholine, pyridine, picoline, N-ethylpyrrolidine, diazabicyclo(4.3.0)-undecene(DBU),1,4-diazabicyclo(2.2.2)octane (DABCO), diazabicyclo(3.2.0)-nonene (DBN), ethyl-diisopropylamine.

The compounds of the formulae II and VI are employed in the ratio 1:1 to 1:1.5 to one another. An approximately equimolar ratio is preferred. The bases are employed in approximately equimolar amounts, relative to the compounds of the formula VI.

After completion of the reaction, the diluent is partly removed (up to about 50%) by distillation, aqueous acid is added to the residue and the compounds of the formula VI are isolated in a manner known per se, by extracting them with a suitable solvent, for example ether or methylene chloride.

The active compounds are suitable for combating pathogenic endoparasites which are encountered in humans and in the keeping and raising of animals with productive, breeding, zoo, laboratory, experimental and pet animals, and have favorable toxicity to warm-blooded animals. They are active against all or individual stages of development of the pests and against resistant and normally sensitive strains. By combating the pathogenic endoparasites disease, cases of death and yield reductions (for example in the production of meat, milk, wool, hides, eggs, honey etc.) should be reduced so that more economical and simpler keeping of animals is possible through the use of the active compounds.

The pathogenic endoparasites include cestodes, trematodes, nematodes and Acantocephalae, in particular:

From the order of the Pseudophyllidea, for example Diphyllobothrium spp., Spirometra spp., Schistocephalus spp., Ligula spp., Bothridium spp., Diphlogonoporus spp..

From the order of the Cyclophyllidea, for example Mesocestoides spp., Anoplocephala spp., Paranoplocephala spp., Monie zia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example Gyrodactylus spp., Dactylogyrus spp., Polystoma spp..

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp..

From the order of the Enoplia, for example Trichuris spp., Capillaria spp., Trichomosoides spp., Trichinella spp..

From the order of the Rhabditia, for example Micronema spp., Strongyloides spp..

From the order of the Strongylida, for example Strongylus spp., Triodontophorus spp., Oesophagodontus spp., Trichonema spp., Gyalocephalus spp., Cylindropharynx spp., Poteriostomum spp., Cyclicocercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example Oxyuris spp., Enterobius spp., Passalurus spp., Syphacia spp., Aspiculuris spp., Heterakis spp..

From the order of the Ascaridia, for example Ascaris spp., Toxascaris spp., Toxocara spp., Parascaris spp., Anisakis spp., Ascaridia spp..

From the order of the Spirurida, for example Gnathostoma spp., Physaloptera spp., Thelazia spp., Gongylonema spp., Habronema spp., Parabronema spp., Draschia spp., Dracunculus spp..

From the order of the Filariida, for example Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example Filicollis spp., Moniliformis spp., Macracanthorhynchus spp., Prosthenorchis spp..

The productive and breeding animals include mammals such as, for example, cattle, horses, sheep, pigs, goats, camels, water buffalo, donkeys, rabbits, fallow deer, reindeer, animals having valuable coats such as, for example, mink, chinchilla, raccoons, birds such as, for example, hens, geese, turkeys, ducks fresh and salt water fish such as, for example, trout, carp, eels, reptiles and insects such as, for example, honey bees and silkworms.

The laboratory and experimental animals include mice, rats, guinea pigs, golden hamsters, dogs and cats.

The pet animals include dogs and cats.

Administration can be carried out both prophylactically and therapeutically.

The administration of the active compounds is carried out directly or enterally, parenterally, dermally or nasally in the form of suitable preparations by treating the environment or with the aid of molded articles containing active compound such as, for example, strips, sheets, tapes, neckbands, ear tags, limb bands and marking devices.

Enteral administration of the active compounds is carried out, for example, orally in the form of powders, tablets, capsules, pastes, drinks, granules, solutions which can be administered orally, suspensions and emulsions, boli, medicated feed or drinking water. Dermal administration can be carried out, for example, in the form of dipping, spraying or pouring-on and spotting-on. Parenteral administration is carried out, for example, in the form of the injection (intramuscular, subcutaneous, intravenous, intraperitoneal) or by implants.

Suitable preparations are: solutions such as injection solutions, oral solutions, concentrates for oral administration after dilution, solutions for use on the skin or in body cavities, pouring-on formulations and gels;

emulsions and suspensions for oral or dermal administration and also for injection; semi-solid preparations;
formulations in which the active compound is processed in an ointment base or in an oil-in-water or water-in-oil emulsion base;
solid preparations such as powders, premixes or concentrates, granules, pellets, tablets, boli, capsules;
aerosols and inhalants, and moulded articles containing active compound.

Injection solutions are administered intravenously, intramuscularly and subcutaneously.

Injection solutions are produced by dissolving the active compound in a suitable solvent and, if necessary, adding additives such as solubilizers, acids,. bases, buffer salts, antioxidants and preservatives. The solutions are sterile filtered and bottled.

Solvents which may be mentioned are: physiologically tolerable solvents such as water, alcohols such as ethanol, butanol, benzyl alcohol, glycerol, propylene glycol, polyethylene glycols, N-methylpyrrolidone, and mixtures of these.

The active compounds may optionally also be dissolved in physiologically tolerable vegetable or synthetic oils which are suitable for injection.

Solubilizers which may be mentioned are: solvents which promote the solution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after previously diluting to the administration concentration. Oral solutions and concentrates are prepared as described above for the injection solutions, it being possible to dispense with sterile working.

Solutions for use on the skin are poured on dropwise, spread on, rubbed in, sprinkled on or sprayed on. These solutions are prepared as described above for the injection solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and methacrylates.

Gels are applied to or spread on the skin or introduced into body cavities. Gels are prepared by adding such a quantity of thickener to solutions which have been prepared as described for the injection solutions that a clear composition having an ointment-like consistency results. The thickeners indicated above are employed as thickeners.

Pouring-on formulations are poured onto or sprinkled onto limited areas of the skin, whereupon the active compound penetrates the skin and acts systemically.

Pouring-on formulations are prepared by dissolving, suspending or emulsifying the active compound in suitable skin-compatible solvents or solvent mixtures. If appropriate, further auxiliaries such as colorants, absorption-promoting substances, antioxidants, light screens and adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone and 2,2-dimethyl-4-oxy-methylene-1,3-dioxolane.

Colorants are all colorants which may be dissolved or suspended and which are permitted for administration to animals.

Absorption-promoting substances are, for example, DMSO, spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, novantisolic acid.

Adhesives are, for example, cellulose derivatives, starch derivatives, polyacrylates, and natural polymers such as alginates and gelatin.

Emulsions may be administered orally, dermally or as injections.

Emulsions are either of the water-in-oil type or the oil-in-water type.

They are prepared by dissolving the active compound either in the hydrophobic or the hydrophilic phase and homogenizing this with the solvent of the other phase with the aid of suitable emulsifiers and, if appropriate, further auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as a caprylic/capric acid biglyceride or triglyceride mixture with vegetable fatty acids of chain length $C_{8-12}$ or other specially selected natural fatty acids, partial glyceride mixtures of saturated or unsaturated fatty acids possibly also containing hydroxyl groups, and mono- and diglycerides of $C_{10}/C_{10}$-fatty acids.

Fatty acid esters such as ethyl stearate, di-n-butyryl adipate, hexyl lauroate, dipropylene glycol pelargonate, esters of a branched fatty acid of medium chain length containing saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as synthetic duck cocoygeal gland fat, dibutyl phthalate, diisopropyl adipate, ester mixtures related to the latter etc.

Fatty alcohols such as isotridecyl alcohol, 2-octyldodecanol, cetylstearyl alcohol and oleyl alcohol.

Fatty acids such as, for example, oleic acid and its mixtures.

Hydrophilic phases which may be mentioned are: water, alcohols such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate and alkylphenol polyglycol ethers; ampholytic surfactants such as di-Na N-lauryl-$\beta$-iminodipropionate or lecithin; anionic surfactants, such as Na lauryl sulphate, fatty alcohol ether sulphates, mono/dialkyl polyglycol ether orthophosphoric acid ester monoethanolamine salt; cationic surfactants such as cetyltrimethylammonium chloride.

Other auxiliaries which may be mentioned are: substances increasing viscosity and stabilizing the emulsion such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions may be administered orally, dermally or as an injection. They are prepared by suspending the active compound in an excipient liquid, if appropriate with the addition of other auxiliaries such as wetting agents, colorants, absorption-promoting substances, preservatives, antioxidants light screens.

Excipient liquids which may be mentioned are all homogeneous solvents and solvent mixtures.

Wetting agents (dispersants) which may be mentioned are the surfactants indicated above.

Other auxiliaries which may be mentioned are those indicated above.

Semi-solid preparations can be administered orally or dermally. They differ from the suspensions and emulsions described above only by their higher viscosity.

In order to prepare solid preparations, the active compound is mixed with suitable excipients, if appropriate with the addition of auxiliaries, and brought into the desired form.

Excipients which may be mentioned are all physiologically tolerable solid inert substances. Those used are inorganic and organic substances. Inorganic substances are, for example, sodium chloride, carbonates such as calcium carbonate, hydrogen carbonates, aluminum oxides, silicic acids, aluminas, precipitated or colloidal silica and phosphates.

Organic substances are, for example, sugars, cellulose, foodstuffs and feeds such as milk powder, animal meal, cereal meal and shreds, and starches.

Auxiliaries are preservatives, antioxidants and colorants which have already been mentioned above.

Other suitable auxiliaries are lubricants and glidants such as, for example, magnesium stearate, stearic acid, talc, bentonites, disintegration-promoting substances such as starch or crosslinked polyvinylpyrrolidone, binders such as, for example, starch, gelatin or linear polyvinylpyrrolidone and dry binders such as microcrystalline cellulose.

The active compounds may also be present in the preparations as a mixture with synergists or with other active compounds which act against pathogenic endoparasites. Such active compounds are, for example, L-2,3,5,6-tetrahydro-6-phenylimidazothiazole, benzimidazole carbamate, praziquantel, pyrantel and febantel.

Ready to use preparations contain the active weight, preferably from 0.1–10 per cent by weight.

Preparations which are diluted before use contain the active compound in concentrations of 0.5–90 per cent by weight, preferably from 5 to 50 per cent by weight.

In general, it has proved advantageous to administer amounts of about 1 to about 100 mg of active compound per kg of body weight per day to attain effective results.

EXAMPLE A

In-vitro nematode test

Caenorhabditis elegans $10^{-4}$ g of active compound are dissolved in 1 ml of water or 0.1 ml of dimethyl sulphoxide (DMSO). This solution was poured onto a replica plate. 2 ml of E. coli suspension to which 10–20 female animals or larvae of Caenorhabditis elegans in 0.5 ml of sterile M9 buffer solution had been added were introduced onto the plate. The E. coli suspension was prepared by adding 1.8 l of sterile M9 buffer solution to 300 ml of an overnight culture of a uracil-dependent E. coli strain.

The test batch was incubated for 7 days at 22° C. and then evaluated. The extent to which the active compound impairs multiplication was evaluated, and the concentration at which multiplication is inhibited is given. The following results were obtained:

TABLE A

| In-vitro nematode test Caenorhabditis elegans ||
|---|---|
| Active compound Example No. | Effective dose (μg/ml) |
| 1 | 100 |
| 2 | 100 |
| 3 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |

EXAMPLE B

In-vivo nematode test

Trichostrongylus colubriformis/sheep

Sheep infected experimentally with Trichostrongylus colubriformis were treated after expiration of the prepatency period. The active compounds were administered orally as the pure active compound in gelatin capsules.

The degree of action is determined by quantitatively counting the worm eggs excreted with the faeces before and after the treatment.

A complete stop to egg laying after the treatment means that the worms have been expelled or damaged such that they no longer produce eggs (effective dose).

Active compounds tested and effective doses can be seen from the following table.

| Active compound Example No. | Effective dose in mg/kg |
|---|---|
| 2 | 10 |
| 13 | 10 |

EXAMPLE C

In-vivo nematode test

Haemonchus contortus/sheep

Sheep infected experimentally with Haemonchus contortus were treated after expiration of the prepatency period. The active compounds were administered orally as the pure active compound in gelatin capsules.

The degree of action is determined by quantitatively counting the worm eggs excreted with the faeces before and after the treatment.

A complete stop to egg laying after the treatment means that the worms have been expelled or damaged such that they no longer produce eggs (effective dose).

Active compounds tested and effective doses can be seen from the following table.

| Active compound Example No. | Effective dose in mg/kg |
|---|---|
| 2 | 10 |
| 10 | 10 |
| 13 | 25 |

Preparation Examples

EXAMPLE 1

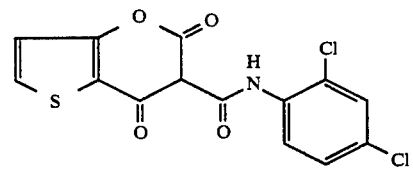

2.55 g (0.015 mol) of thieno-[3.2]-7-hydroxy-pyran-5-one are taken up in 20 ml of DMSO. 1.5 g of triethylamine are then added slowly and, after this, 2.82 g (0.015 mol) of 2,4-dichlorophenyl isocyanate are added.

The mixture is stirred for 12 hours at room temperature and then poured into 75 ml of water which has previously been acidified using 4.5 ml of conc. hydrochloric acid.

The mixture is stirred for 30 minutes at 0° C., and the precipitate is filtered off with suction and stirred with 100 ml of methanol-methylene chloride solution (1:1). The product is filtered off with suction and dried.

Yield: 4.3 g (80.5%)
m.p.: 261° C.
IR (KBr): 1705; 1590; 1540; 1045
NHR (DMSO): 7.38 d (1); 7.5 dd (1); 7.63 d (1); 8.1 d (1); 8.3 dd (1); 11.65 s (1)

The following are obtained analogously:

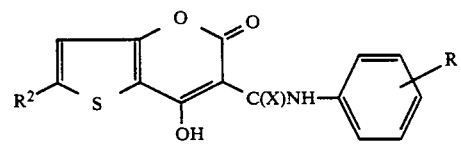

| Ex. No. | R² | X | R | m.p. [°C.] |
|---|---|---|---|---|
| 2 | H | O | 4-Cl | 220 |
| 3 | H | O | 3-Cl, 4-CF₃ | 230 |
| 4 | H | O | 2,4,5-Cl₃ | 254–255 |
| 5 | H | O | 2,3,4,5,6-Cl₅ | 251 |
| 6 | H | O | 4-OC₂H₅ | 183–184 |
| 7 | H | O | 3-Cl | 210–211 |
| 8 | H | O | 3,4-Cl₂ | 249–250 |
| 9 | H | O | 3-CF₃ | 190 |
| 10 | H | O | 4-SCF₃ | 218–220 |
| 11 | H | O | 3-Cl, 4-SCF₃ | 204–205 |
| 12 | H | O | 3-Cl, 4-CH₃ | 203–204 |
| 13 | H | O | 4-CH₃ | 186 |
| 14 | phenyl | O | 4-Cl | 257–258 |
| 15 | H | O | 4-OCF₃ | 203–204 |
| 16 | phenyl | O | 4-CH₃ | 274 |
| 17 | CH₃ | O | 4-Cl | 214 |
| 18 | H | O | 3 Cl, 4-OCF₃ | 167 |
| 19 | CH₃ | O | 3-CF₃ | 202–203 |
| 20 | H | O | 3-SO₂F | 230 |
| 21 | CH₃ | O | 4-OCF₃ | 210 |
| 22 | CH₃ | O | 3-Cl, 4-OCF₃ | 214 |
| 23 | CH₃ | O | 4-SCF₃ | 221 |
| 24 | CH₃ | O | 3-SO₂F | 254–255 |
| 25 | CH₃ | O | 3-Cl, 4-SCF₃ | 226 |
| 26 | CH₃ | O | 3-Cl, 4-SF₂Cl | 216 |
| 27 | CH₃ | O | (4-O-tolyl-OCF₂CF₃) | 212 |
| 28 | CH₃ | O | (4-O-phenyl-3-CF₃) | 208 |
| 29 | CH₃ | O | 2-Cl, 4-CF₃ | 240 |
| 30 | CH₃ | O | 2,4,5-Cl₃ | 231 |
| 31 | CH₃ | O | 3-Cl | 211 |
| 32 | CH₃ | O | 4-CH₃ | 238 |
| 33 | CH₃ | S | H | 181–182 |

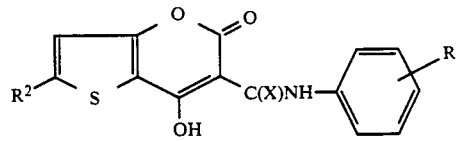

| Ex. No. | R² | X | R | m.p. [°C.] |
|---|---|---|---|---|
| 34 | CH₃ | O | 4-Cl | 221–222 |
| 35 | CH₃ | O | 2,4-Cl₂ | 225–226 |
| 36 | CH₃ | O | 3,4-Cl₂ | 227 |
| 37 | CH₃ | O | 2,4,5,6-Cl₅ | 180 |
| 38 | CH₃ | O | 3-Cl, 4-SCF₃ | 224 |
| 39 | CH₃ | O | 3-NO₂ | 240 |
| 40 | CH₃ | O | 4-OC₂H₅ | 216 |
| 41 | H | S | 4-Cl | 207–208 |
| 42 | H | O | 3-NO₂ | 227–228 |
| 43 | phenyl | O | 2-Cl, 4-CF₃ | 198–199 |
| 44 | H | O | 3-Cl, 4-SCF₃ | 178–180 |
| 45 | H | O | (4-O-tolyl-OCF₂CF₃) | 205 |
| 46 | H | O | 4-F | 220–221 |
| 47 | H | O | 4-Br | 228–229 |
| 48 | CH₃ | O | 4-F | 190–191 |

Examples of the preparation of the starting materials a) Preparation of thieno-[3.2]-7-hydroxypyran-5-one

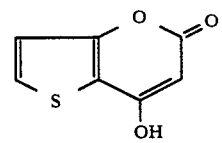

2.07 g (0.00966 mol) of 2-ethoxycarbonylaceto-3-hydroxythiophene are heated to reflux for 1 hour with 50 ml of absolute xylene. During the course of this, the xylene is slowly stripped off, and the product precipitates during the course of this as a solid and is filtered off with suction.

Yield: 0.4 g (22%)
m.p.: 223°–225° C.

The following compounds were prepared analogously:

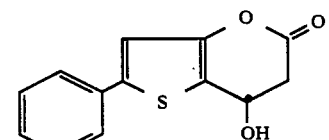

C₁₃H₈O₃S m.p.: 214°–215° C.
NMR (CDCl₃): 5.6 s (1), 7.2 s (1), 7.4–7.6 m (s)
IR (KBr): 1640; 1560; 1480; 1400

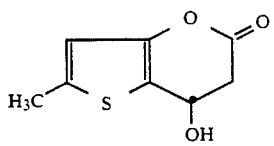

C<sub>8</sub>H<sub>8</sub>O<sub>3</sub>S m.p.: 210°–212° C.
NMR (CDCl<sub>3</sub>): 1.6 s (3), 7.3 s (1)
IR (KBr): 1680; 1560; 1510; 1330
MS: 182 (65%); 140 (100%); 112 (30%)

b) Preparation of 3-ethoxycarbonylaceto-3-hydroxythiophene

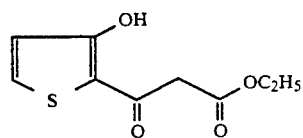

4.8 g (0.0337 mol) of 2-aceto-3-hydroxythiophene are heated to 90°–100° C. in 150 ml of diethyl carbonate. 5 g of sodium are then added in small pieces. The mixture is stirred at 90°–100° C. for 15 hours. Some ethanol is added to decompose sodium residues. For working up, the mixture is extracted by shaking twice with 75 ml of water, then the aqueous phase is acidified using 10 ml of conc. HCl, extracted by shaking 3 times with 50 ml of ether each time, dried and concentrated in vacuo. For the preliminary purification, the residue is distilled in vacuo and the fraction between 70° and 100° C. (0.5 torr, educt) and between 113° and 118° C. (0.3 torr, product) is collected.

For purification, this is chromatographed using ethyl acetate/cyclohexane 1:1.

Yield: 0.5 g (6.9%).

c) Preparation of 2-aceto-3-hydroxythiophene

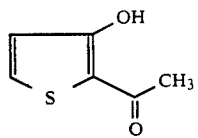

4.65 g of NaOCH<sub>3</sub> suspended in 100 ml of toluene. A suspension of 7.6 g (0.0843 mol) of acetonylmercaptan in 150 ml of toluene is then added. 7.1 g (0.0843 mol) of methyl propiolate are then added dropwise. The mixture is heated to reflux for 1 hour. After cooling, a solution of 4.5 ml of conc. H<sub>2</sub>SO<sub>4</sub> in 120 ml of water is added dropwise. The toluene phase is separated off and washed 3 times with 50 ml of water each time, dried and concentrated. The mixture is distilled, and the crude fraction between 85° C. and 90° C. at 12 torr is collected. Weight of the crude product: 6 g. The crude product is poured into 48 ml of 1 N NaOH and extracted by shaking with ether. The aqueous phase is acidified using 2 N HCl and extracted with ether. After drying and concentrating, the residue is triturated with ether.

Yield: 1.2 g (10%)
m.p.: 48°–50° C.

The following compound was prepared analogously:

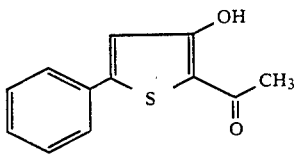

C<sub>12</sub>H<sub>10</sub>O<sub>2</sub>S m.p.: 93°–94° C.
NMR (CDCl<sub>3</sub>): 2.5 s (3); 2.7 s (3); 6.65 s (1)
IR (KBr): 1600; 1480; 1420; 1370; 1340

Preparation of 5-methyl-hydroxythiophene

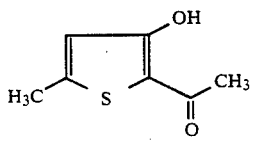

C<sub>7</sub>H<sub>8</sub>O<sub>2</sub>S 156.3 g/mol

Process a)

42.1 (0.78 mol) of sodium methoxide are suspended in 1000 ml of toluene. 70.3 g of 2,5-dihydroxy-2,5-dimethyl-1,4-dithiane (0.78 mol) and 190 g (1.28 mol) of ethyl β-chloro-crotonate are then added.

The mixture is then refluxed for 2 hours. It is then cooled and a solution of 41.7 ml of conc. H<sub>2</sub>SO<sub>4</sub> in 1100 ml of water is added to the reaction mixture.

The organic phase is separated, and the aqueous phase is subsequently extracted with toluene. The combined organic phases are washed with water and then dried over Na<sub>2</sub>SO<sub>4</sub>.

After filtering off the drying agent, the solvent is stripped off. The residue is taken into 450 ml of 1 N NaOH solution and extracted once with ether. The aqueous phase is acidified using 2 N HCl and extracted with ether. The organic phases are dried over Na<sub>2</sub>SO<sub>4</sub>. After separating the drying agent and stripping off the solvent, the residue is crystallized by triturating with ether.

Yield: 20 g (16%)
m.p.: 74°–75° C.
KR (KBr): 1490; 1440; 1220; 1040
NMR (CD Cl<sub>3</sub>): 2.3 s (3); 2.45 d (3); 6.5 d (1); 11.7 s broad (1)
MS: 156 (100%); 141 (100%)

Process b)

A solution of 2.92 g (0.02 mol) of ethyl β-thioacetate, dissolved in 10 ml of absolute benzene, is added dropwise under a nitrogen atmosphere to a solution of 0.025 mol of sodium hydride in 50 ml of absolute benzene.

The mixture is then refluxed for 30 minutes.

2.78 g (0.03 mol) of chloroacetone, dissolved in 20 ml of absolute benzene, are then added dropwise and the mixture is refluxed for a further 3 hours. The mixture is then poured into ice water and acidified. The organic phase is separated and the solvent is stripped off.

The residue is taken up in 100 ml of absolute DMSO. 0.03 mol of sodium hydride are added under a nitrogen atmosphere, then the mixture is stirred for 2 hours. The mixture is then added to water and acidified. The aqueous phase is extracted with ether and the organic phase is dried over Na<sub>2</sub>SO<sub>4</sub>.

After stripping off the solvent, the product is purified by chromatography (eluent: ethyl acetate/cyclohexane 1:1).

Yield: 470 mg (15%)

The following compound was prepared analogously:

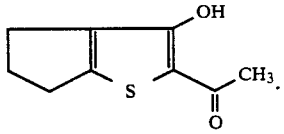

$C_9H_{10}O_2S$ (pale yellow oil)

IR (KBr):

NMR (CDCl$_3$): 2.3 s (3); 2.4–2.5 m (2); 2.6–2.7 m (2); 2.85–2.95 m (2); 11.8 m (1)

MS: 182 (56%); 167 (100%)

It will be appreciated that the instant specification is set forth by way of illustration and not limitation, and that various modifications and changes may be made without departing from the spirit and scope of the present invention.

What is claimed is:

1. A substituted thienopyranone of the formula

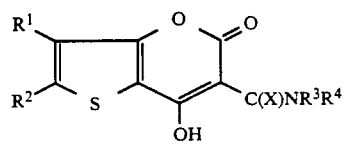

in which

X represents O or S, $R^1$ and $R^2$ represent hydrogen, halogen, CN, NO$_2$, C$_{1-6}$-alkyl, benzyl, C$_{1-4}$-alkylcarbonyl, C$_{1-4}$-alkoxycarbonyl, or phenyl optionally substituted by radial (A) alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, alkylenedioxy having 1 or 2 carbon atoms, halogen-substituted alkylene=dioxy having 1 or 2 carbon atoms and 1 to 4 halogen atoms, halogen, cyano, nitro, dialkylamino having 1 to 4 carbon atoms per alkyl group, alkylcarbonyl having 2–4 carbon atoms, carbalkoxy having 2 to 4 carbon atoms, alkylsulphonyl having 1 to 4 carbon atoms, phenylsulphonyl, naphthylsulphonyl, or phenyl, naphthyl, phenoxy, naphthoxy, phenylthio or naphthylthio, $R^3$ represents C$_{1-6}$-alkyl, or phenyl optionally substituted by C$_1$–C$_4$-alkyl, C$_1$–C$_4$-alkoxy, C$_1$–C$_4$-halogenoalkoxy, C$_1$–C$_4$-halogenoalkylthio, C$_1$–C$_4$-alkylthio, halogenosulphonyl, C$_1$–C$_4$-halogenosulphonyl, C$_1$–C$_4$-halogenoalkyl, methylenedioxy or ethylenedioxy which are optionally substituted by fluorine or chlorine, halogen, CN, NO$_2$, or phenoxy which is optionally substituted by one of the abovementioned radicals (A), and $R^4$ represents hydrogen or C$_{1-4}$-alkyl.

2. A compound according to claim 1, in which $R^1$ and $R^2$ represent hydrogen, chlorine, bromine, CN, C$_1$–C$_4$-alkyl, acetyl, methoxycarbonyl, ethoxycarbonyl, or optionally substituted phenyl, $R^3$ represents optionally substituted phenyl, the optional phenyl substituents for $R^1$, $R^2$ and $R^3$ being radial (B) C$_1$–C$_4$-alkyl, C$_1$–C$_4$-alkoxy, C$_1$–C$_4$-ahlogenoalkoxy, C$_1$–C$_4$-halogenoalkylthio, C$_1$–C$_4$-alkylthio, halogenosulphonyl, C$_1$–C$_4$-halogenoalkyl, methylenedioxy or ethylenedioxy which are optionally substituted by fluorine or chlorine, halogen, CN, NO$_2$, or phenoxy which is optionally substituted by one of the abovementioned radicals (B) and $R^4$ represents hydrogen.

3. A compound according to claim 1, in which

X represents oxygen, $R^1$ represents hydrogen, $R^2$ represents phenyl which is optionally substituted by halogen, C$_{1-4}$-alkyl, C$_{1-4}$-halogenoalkyl or C$_{1-4}$alkoxy, $R^3$ represents phenyl which is optionally substituted by halogen, C$_{1-4}$-alkyl, C$_{1-4}$-halogenoalkyl, C$_{1-4}$-alkoxy C$_{1-4}$-alkylmercapto, C$_{1-4}$-halogenoalkylmercapto, or C$_{1-4}$-alkoxycarbonyl, and $R^4$ represents hydrogen.

4. A parasiticidal composition comprising a parasitically effective amount of a compound according to claim 1 and a diluent.

5. A method of combating parsites which comprises applying to such parasites a parasiticidally effective amount of a compound according to claim 1.

* * * * *

UNITED STATES PATENT AND TRADEMARK OFFICE
CERTIFICATE OF CORRECTION

PATENT NO. : 5,095,032

DATED : March 10, 1992

INVENTOR(S) : Bertram et al.

It is certified that error appears in the above-identified patent and that said Letters Patent is hereby corrected as shown below:

Title Page item [56]   U.S. PATENT DOCUMENTS:   Delete " 587,786 " and substitute -- B587,786 --

Col. 22, line 24   Delete " ahlogenoalkoxy " and substitute -- halogenoalkoxy --

Signed and Sealed this

Twenty-first Day of December, 1993

Attest:

BRUCE LEHMAN

*Attesting Officer*   *Commissioner of Patents and Trademarks*